US006179775B1

(12) United States Patent
Thompson

(10) Patent No.: US 6,179,775 B1
(45) Date of Patent: Jan. 30, 2001

(54) DEVICE TO ENCHANCE CLITORAL STIMULATION DURING INTRAVAGINAL INTERCOURSE

(75) Inventor: Ronald J. Thompson, Ft. Thomas, KY (US)

(73) Assignee: 40 J's LLC, Fort Thomas, KY (US)

( * ) Notice: Under 35 U.S.C. 154(b), the term of this patent shall be extended for 0 days.

(21) Appl. No.: 09/340,227

(22) Filed: Jul. 1, 1999

(51) Int. Cl.[7] .......... A61F 5/00
(52) U.S. Cl. .......... 600/38
(58) Field of Search .......... 600/38, 29, 30, 600/31

(56) References Cited

U.S. PATENT DOCUMENTS 4,139,006 * 2/1979 Corey .......... 600/29
5,386,836 * 2/1995 Biswas .......... 600/29

* cited by examiner

*Primary Examiner*—Cary O'Connor
*Assistant Examiner*—Brian Szmal
(74) *Attorney, Agent, or Firm*—Don Halgren

(57) ABSTRACT

The present invention includes an apparatus for the increased female clitoral stimulation. The apparatus comprises a foraminous, elongated, generally triangularly shaped pad having an anterior portion arranged to support and engage the ventral aspect of the clitoris and lie beneath the labia minora. The pad has an outer peripheral contour so as to seat within the female vestibule. The pad is comprised of a plurality of layers of flexible material. The pad has an uppermost layer of soft flexible material and an intermediate layer of generally semi-rigid material and a lower layer of an adhesive material.

20 Claims, 2 Drawing Sheets

DEVICE TO ENCHANCE CLITORAL STIMULATION DURING INTRAVAGINAL INTERCOURSE

BACKGROUND OF THE INVENTION

1. Field of the Invention

This invention relates to the field of devices or appliances utilized to stimulate female genitalia during sexual intercourse. More specifically, the present invention relates to a removable externally replaceable pad for installation in the external genitalia of a human female.

2. Anatomy and Physiology of Female Sexual Stimulation

The clitoris is the female structure analogous to the male penis and is primarily responsible for the female sexual response and her excitation. As with the male penis, the clitoris contains both sensory nerves and erectile tissue. The erectile tissue is responsible for the enlargement of the clitoris, two to four-fold as the clitoris engorges with blood during the arousal phase of female sexual stimulation. Once enlarged maximally, the clitoris is in the excitation state, and with continued repetitive stimulation of the sensory nerves of the clitoris, multiple orgasms occur. Orgasms are the rhythmic contraction of the muscular pelvis including the vaginal, balbocavernososus, pasococoxygeal and levator ani muscles. Once an orgasm has occurred, relaxation of the pelvic muscles automatically allows another orgasm to occur from the continuous stimulation of the enlarged clitoris. This repetitive action of multiple orgasms from the excitation plateau is unique to females.

Stimulation of the clitoris can be digital, vibrating, or displacement in nature. The clitoris is positioned at the dorsal apex of the female genital area and is covered by the clitoral hood, but not attached to the clitoral hood. The clitoral hood is actually an inverted "V" and continues at the labia minora that laterally outline the entrance to the vagina. With intravaginal intercourse, the penis causes a lateral stretching of the labia minora and the downward pulling of the clitoral hood. The in-and-out movement of the penis relative to the vaginal entrance causes a pulling on the clitoral hood and affects clitoral stimulation. During penetration, the clitoral hood is further tensioned. In penile withdrawal, the clitoral hood is relaxed and returned to the tensioned state. Therefore, the two mechanisms: the lateral stretching of the labia minora causing the tensioning of the clitoral hood against the clitoris, and the pulling of the clitoral hood against the dorsal clitoris during penetration causes clitoral stimulation. All of the stimulation is on the dorsal aspect of the clitoris and becomes more pronounced as the clitoris becomes erect and enlarged. This dorsal stimulation is unopposed, for the ventral aspect of the clitoris is unsupported, especially in the erect state.

BRIEF SUMMARY OF THE INVENTION

The present invention is a proposed device to enhance clitoral stimulation during intravaginal intercourse and would serve two functions. One preferred embodiment of the present invention would comprise a slightly elongated pad with an adhesive backed portion which would support the ventral aspect (under carriage) of the clitoris with a "U" shaped notch or a flattened end somewhat rounded surface at one end thereof. This pad would prevent the downward displacement of the engorged clitoris with the downward motion of the clitoral hood. The second function, in addition the support function, would be accomplished by the somewhat elongated pad transferring stimulation from the dorsal aspect of the penis to the ventral aspect of the clitoris.

During penile penetration of the vagina, the clitoris would be stimulated by the entrapment of the clitoris between the downward tensioned clitoral hood and the upwardly supporting adherent stimulating device. Stimulation would also be directly transferred from the interaction of the bottom of the elongated pad with a mobile penis and the ventral aspect of the clitoris. The direct stimulation of the clitoris would be vibratory in nature since the dorsal aspect of the penis is not perfectly smooth but ridged when erect.

The present invention comprises a multi-layered pad arrangement of elongated yet generally triangular configuration having a truncated or an anterior end. The under side of the pad would be coated with a hydrophilic adhesive, which would hold the device in place and not interact, during female sexual arousal with a serum transudate that lubricates the entire female vulva and vagina. Such a hydrophilic adhesive would be non-allergenic but would ensure adherence of the device against the female vestibule, as long as is needed. A flexible multi-layered pad of the present invention may have a middle layer of either a foam, a flexible foraminous plastic or a thin flexible foranamous shaped memory alloy strip to both to serve a supportive function to the central clitoris and to transfer vibratory stimulation from the penis to the central clitoris.

The supportive "middle" layer could be the actual interface between a soft sponge-like outer surface of the device and the adhesive innermost layer. This interface would create an adhesive permeated layer of the spongy surface that would act as a supportive or a stiffening element.

The outermost surface of the pad of the present invention will be comprised of a smooth via flexible yet spongy material with the outward feel of artificial skin and a shape to conform to the anterior genital area. The present inventive device would have a somewhat elongated, generally inverted "V" shape in one embodiment with a round notch at the apex of the "V", to interface with the under carriage of the clitoris for 130 to 180 degrees. The edges of the anterior end of the pad would be rounded and inwardly tapered more toward the top lateral edges to accommodate and allow labial minora movement without friction. The pad of the present invention would be thicker both in the center and at the base of the "V", to permit a larger surface for interfacing with the penis during intercourse. The layer of adhesive could be surrounded by a perimeter of non-adhesive comprising an intermediate layer of the pad that comprises the semi-rigid internal support which functions as a stiffening or conductive element. The multi-layered device would be between two and ten millimeters thick, and the anterior end thereof being the thinnest adjacent to the "V" shaped slot, to fit beneath the libia minora. The width of the present pad would be between 10 and 30 millimeters wide at the inferior end thereof.

The invention thus comprises an apparatus for the increased female clitoral stimulation. The pad comprises a foraminous, elongated, triangularly shaped pad having an anterior portion arranged to support the ventral aspect of the clitoris and lie beneath the labia minora, said pad having an outer peripheral contour so as to seat within the female vestibule. The pad is comprised of a plurality of layers of flexible material. The pad has an uppermost layer that could be of fluid permeable material. The pad could have an intermediate layer of fluid permeable generally rigid material. The material of the intermediate layer is selected from the group comprised of: open cell foam, shaped memory metal, fibrous plastic and fiber board or silicon. The pad has a lowermost layer of adhesive. The adhesive layer is a hydrophilic adhesive. The lower layer may be of smaller dimension than the intermediate layer. The anterior end of the pad has a generally "U" shaped notch arranged therein to engage the ventral aspect of a clitoris therewith. The "U" shaped notch is arranged to engage between 130 degrees and 180 degrees of the ventral aspect of a clitoris. An electronic telemetry device may be arranged within the pad. The electronic telemetry device may be selected from the group comprising: a temperature sensor, a moisture sensor, an oscillator and a signal transmitter/receiver. The pad may be comprised of a tubular frame with on open central portion. The tubular frame may be comprised of a shape memory alloy. The invention may also comprise a method of improving the clitoral stimulation of a female during intravaginal intercourse, comprising one or more of the following steps as: providing a foraminous pad of generally triangular outer contour; and placing an anterior portion of the pad against the ventral aspect of a clitoris; placing a "U" shaped notch in the anterior portion of the pad; forming the pad of a plurality of layers of fluid permeable material; coating a lowermost portion of the pad with a hydrophillic adhesive; and placing an electronic telemetry device within the pad.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
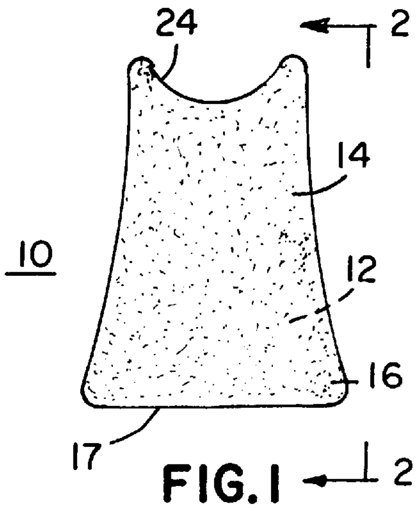
FIG. 1 is a plan view of the stimulation device constructed according the principles of the present invention.

Referring now to the drawings in detail, and FIG. 1 in particular, there is shown the present invention comprising is a generally elongated, thin, planar, flexible, foraminous, triangularly shaped clitoral stimulation pad 10 with a hydrophillic adhesive coated lowermost layer 12. The pad 10 has a narrow anterior or first end 14 and a wider second end 16. As may be seen in FIG. 2, a portion of the pad 10 is shown in partial section, disclosing an upper layer 18 of smooth open cell plastic, and an internal layer 20 of foraminous, slightly rigid material such as fiberous paper, plastic or a shape memory NiTi alloy such as Nitinol, to add slight rigidity and formability to the pad 10. A tab 22 may be arranged to extend off of the uppermost layer 18 to permit attachment or removal of the pad 10 from the wearer.

Figure 3:
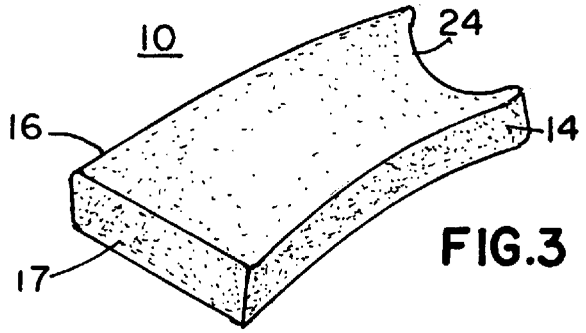
FIG. 3 is an isometric view of the pad of the present invention.

As is shown in FIGS. 1 and 3, the first end 14, which is arranged to support the central aspect (under carriage) of the clitoris, has a "U" shaped notch 24 disposed thereat. The notch 24 would touchingly engage and extend about 120 degrees to about 180 degrees around the ventral aspect of the clitoris. The pad 10 would support and thus prevent the downward displacement of the engorged clitoris with the downward motion of the clitoral hood. The second function, in addition the support function, would be accomplished by the somewhat elongated pad 10 transferring stimulation from the dorsal aspect of the penis to the ventral aspect of the clitoris. During penile penetration of the vagina, the clitoris would be stimulated by the entrapment of the clitoris between the downward tensioned clitoral hood and the upwardly supporting adherent stimulating pad 10. Stimulation would also be directly transferred from the interaction of the bottom of the elongated pad 10 with a mobile penis and the ventral aspect of the clitoris.

The adhesive coat 12 on the lower side of the pad is a hydrophilic adhesive, which would hold the device in place and not interact, during female sexual arousal with a serum transudate that lubricates the entire female vulva and vagina. Such a hydrophilic adhesive would be non-allergenic but would ensure adherence of the device against the female vestibule, as long as is needed.

Figure 2:
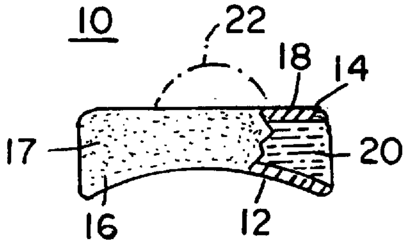
FIG. 2 is a view taken along the lines 2—2 of FIG. 1.

The supportive "middle" layer 20 in the preferred embodiment as shown in FIG. 2, may be the actual interface between a soft sponge-like outer surface of the device and the adhesive lowermost layer 12. This interface would create an adhesive permeated layer of the spongy surface that would act as a supportive or a stiffening element.

The upper outermost surface layer 18 of the pad 10 is preferably comprised of a smooth, flexible, yet spongy material with the outward feel of artificial skin and a shape to conform to the interior genital area. The edges of the anterior end of the pad would be rounded and inwardly tapered more toward the top lateral edges to accommodate and allow labial minora movement without friction. As may also be seen in FIG. 1, the pad 10 may be thicker both in the center and at the second end 16, to permit a larger surface 17 for interfacing with the penis during intercourse. The layer of adhesive 12 on the "lower" surface of the pad 10 may be surrounded by a perimeter of a flexible, non-adhesive material comprising the intermediate layer 20 of the pad 10 that comprises the semi-rigid internal support which functions as a stiffening or conductive element. The multi-layered pad 10 is preferably between two and ten millimeters thick, and the anterior end 14 being the thinnest adjacent to the "V" shaped slot, to fit beneath the labia minora. The width of the present pad 10 is preferably between 10 and 30 millimeters wide at the posterior and thereof.

Figure 4:
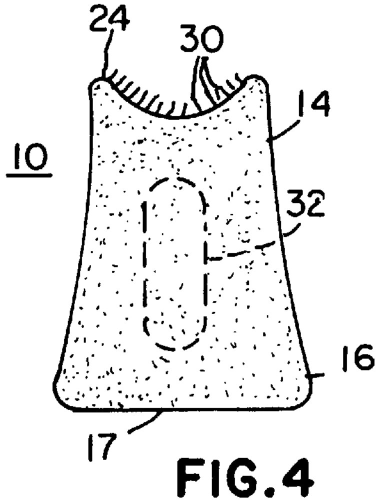
FIG. 4 is a plan view of a further embodiment of the pad of the present invention.

A still further embodiment is shown in FIG. 4, showing the pad 10 with a plurality of minute, thin, flexible projections 30 extending off of the periphery of the generally "U" shaped notch 24. The projections 30 serve to frictionally engage the ventral aspect of the clitoris during engorgement thereof. An electronic telemetry device 32 may be disposed below the inner layer 18, as also represented in FIG. 4. Such telemetry device 32 may be comprised of one or more of the following, such as a temperature or moisture sensor, an oscillatory member and a miniature chip transmitter/receiver.

Figure 5:
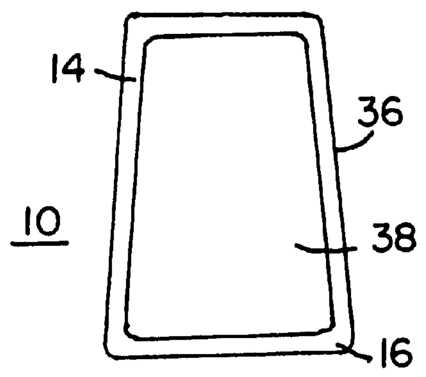
FIG. 5 is a plan view of yet a further embodiment of the pad of the present invention.

FIG. 5 discloses the pad 10 configured as a tubular structure 36 constructed from a yieldable material of plastic or a metal such as the aforementioned NiTi shaped memory alloy. The pad 10 has its anterior portion 14 and its posterior portion 16, and is comprised of the tubular structure 36 has an open mid-portion 38, and does not have the multi-layer components of the earlier embodiments. Such a structure 36 is shaped to conform to the peripheral contour of the aforementioned embodiments.

Figure 6:
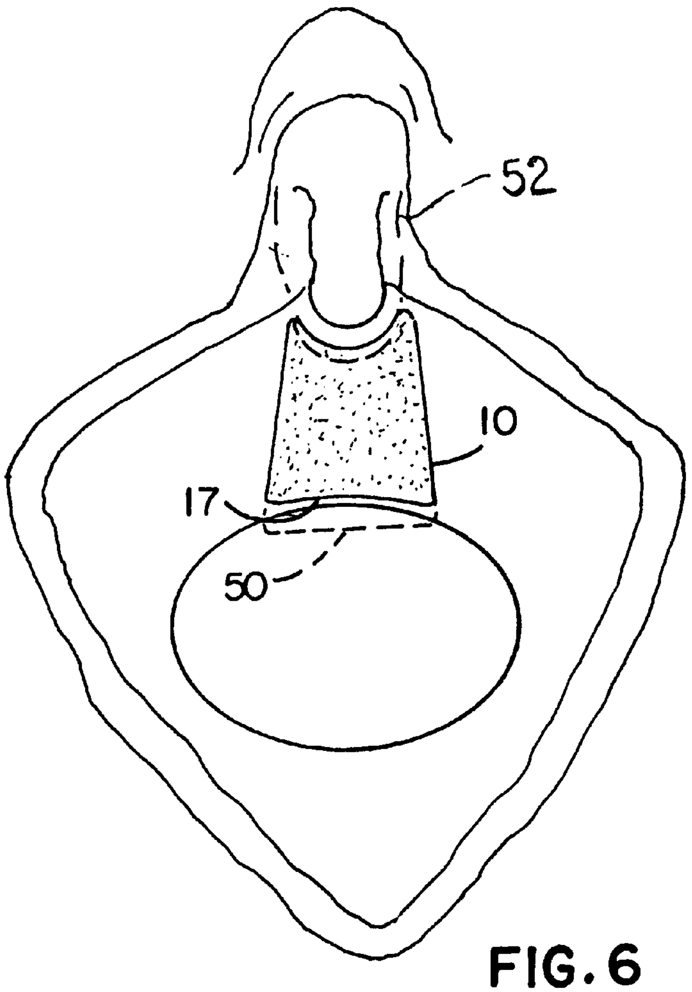
FIG. 6 is a representation of the pad mated within the external genitalia of a female.

FIG. 6 shows the arrangement of the pad 10 of the present invention disposed within the female genitalia. The pad 10 is displaced posteriorly somewhat as indicated by the dashed lines 50, when the clitoris is engorged and excited, as represented by the dashed lines 52.

I claim:

1. An apparatus for the increased female clitoral stimulation, comprising a foraminous, elongated, triangularly shaped pad having an anterior portion arranged to support the ventral aspect of the clitoris and lie beneath the labia minora, said pad having an outer peripheral contour so as to seat within the female vestibule.

2. The apparatus as recited in claim 1, wherein said pad is comprised of a plurality of layers of flexible material.

3. The apparatus as recited in claim 2, wherein said pad has an uppermost layer of fluid permeable material.

4. The apparatus as recited in claim 2, wherein said pad has an intermediate layer of fluid permeable generally rigid material.

5. The apparatus as recited in claim 4, wherein said material of said intermediate layer is selected from the group comprised of: open cell foam, shaped memory metal, fibrous plastic and fiber board.

6. The apparatus as recited in claim 2, wherein said pad has a lowermost layer of adhesive.

7. The apparatus as recited in claim 6, wherein said adhesive layer is a hydrophilic adhesive.

8. The apparatus as recited in claim 6, wherein said lower layer is of smaller dimension than said intermediate layer.

9. The apparatus as recited in claim 1, where said anterior end of said pad has a generally "U" shaped notch arranged therein to engage the ventral aspect of a clitoris therewith.

10. The apparatus as recited in claim 9, wherein said "U" shaped notch is arranged to engage between 130 degrees and 180 degrees of the ventral aspect of a clitoris.

11. The apparatus as recited in claim 1, wherein an electronic telemetry device is arranged within said pad.

12. The apparatus as recited in claim 11, wherein said electronic telemetry device is selected from the group comprising: a temperature sensor, a moisture sensor, an oscillator and a signal transmitter/receiver.

13. The apparatus as recited in claim 1, wherein said pad is comprised of a tubular frame with an open central portion.

14. The apparatus as recited in claim 13, wherein said tubular frame is comprised of a plastic material.

15. The apparatus as recited in claim 13, wherein said tubular frame is comprised of a shape memory alloy.

16. A method of improving the clitoral stimulation of a female during intravaginal intercourse, comprising the steps of:

providing a foraminous pad of generally triangular outer contour; and placing an anterior portion of said pad against the ventral aspect of a clitoris.

17. The method as recited in claim 16, including the step of:

placing a "U" shaped notch in said anterior portion of said pad.

18. The method as recited in claim 16, including the step of:

forming said pad of a plurality of layers of fluid permeable material.

19. The method as recited in claim 18, including the step of:

coating a lowermost portion of said pad with a hydrophillic adhesive.

20. The method as recited in claim 18, including the step of:

placing an electronic telemetry device within said pad.

* * * * *